United States Patent
Maki et al.

(10) Patent No.: US 7,139,600 B2
(45) Date of Patent: Nov. 21, 2006

(54) BIOPHOTOMETER

(75) Inventors: Atsushi Maki, Fuchu (JP); Michiyuki Fujiwara, Kashiwa (JP); Jacques Mehler, Trieste (IT); Ghislaine Dehaene-Lambertz, Paris (FR); Marcela Pena, Vina del Mar (CL)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 503 days.

(21) Appl. No.: 10/450,895

(22) PCT Filed: Jan. 18, 2002

(86) PCT No.: PCT/JP02/00325

§ 371 (c)(1),
(2), (4) Date: Oct. 7, 2003

(87) PCT Pub. No.: WO02/080777

PCT Pub. Date: Oct. 17, 2002

(65) Prior Publication Data

US 2004/0054271 A1    Mar. 18, 2004

(30) Foreign Application Priority Data

Apr. 2, 2001 (JP) .............................. 2001-102806

(51) Int. Cl.
*A61B 5/00*    (2006.01)
(52) U.S. Cl. ..................... 600/344; 600/473; 600/476

(58) Field of Classification Search ................ 600/310, 600/322, 323, 340, 344, 473, 476
See application file for complete search history.

(56) References Cited

U.S. PATENT DOCUMENTS

| 5,090,415 | A | * | 2/1992 | Yamashita et al. | ........... 600/476 |
| 5,529,065 | A | * | 6/1996 | Tsuchiya | .................... 600/310 |
| 5,803,909 | A | | 9/1998 | Maki et al. | |
| 6,240,309 | B1 | * | 5/2001 | Yamashita et al. | .......... 600/476 |
| 6,577,884 | B1 | * | 6/2003 | Boas | .......................... 600/310 |

FOREIGN PATENT DOCUMENTS

| JP | 57-115232 | 7/1980 |
| JP | 63-275323 | 5/1987 |
| JP | 4-81375 | 7/1990 |
| JP | 6-44510 | 4/1993 |
| JP | 9-98972 | 10/1995 |
| JP | 9-135825 | 11/1995 |
| JP | 9-149903 | 11/1995 |

\* cited by examiner

*Primary Examiner*—Eric F. Winakur
(74) *Attorney, Agent, or Firm*—Reed Smith LLP; Stanley P. Fisher, Esq.; Juan Carlos A. Marquez, Esq.

(57) ABSTRACT

The present invention provides an optical measurement device of biological tissue having a probe attachable to a moving part of a living body with a high curvature in biophotometry. A member having a high flexibility and a high friction coefficient is disposed on a surface for contact with the living body. In addition, a device for light irradiation and a device for collection of light are fixed with an elastic material for uniform pressure application. The resulting double structure or double layer has solved a problem.

10 Claims, 4 Drawing Sheets

2-1

2-2

BIOPHOTOMETER

TECHNICAL FIELD

The present invention relates to an optical measurement device of biological tissue for measuring, by using light, a substance of metabolism within a living body.

BACKGROUND ART

In biomeasurement using light, an apparatus for measuring the activity of a living body by using visible to near infrared light is disclosed in, e.g., Japanese Patent Application Laid-Open No. 57-115232 or Japanese Patent Application Laid-Open No. 63-275323. In addition, an invention pertaining to image measurement technology for the activity of a brain (optical topography (R)), which has been achieved through the application of the present principle of measurement, is proposed in Japanese Patent Application Laid-Open No. 9-98972.

Each of these inventions irradiates a living body with light by using an optical wave-guiding device represented by an optical fiber or the like and collects and measures the light scattered within the living body (hereinafter shortly referred to as the living-body scattered light) at a position several millimeters to several centimeters apart. From the measured intensity of the living-body scattered light, the concentration of a substance of light absorption within the living body represented by oxygenated hemoglobin or deoxygenated hemoglobin or a value corresponding to the concentration is determined. In determining the concentration of the substance of light absorption or the value corresponding to the concentration, the light absorption characteristic of the objective substance of light absorption, which corresponds to the wavelength of the irradiated light, is used. In the case of measuring a deep portion in a living body, light with a wavelength in the range of 650 nm to 1300 nm, which is high in living body penetration, is used normally.

In biophotometry, a device for irradiating a subject (living body) with light (hereinafter referred to as the device for light irradiation) and a device for collecting light propagated through the inside of the living body (hereinafter referred to as the device for collection of light) are provided. As the device for light irradiation and the device for collection of light, an optical wave-guide represented by an optical fiber or a bundle of optical fibers is provided in most cases. A pair of optical wave-guides for light irradiation and for collection of light form a minimum unit representing one measurement position (hereinafter referred to as the light-irradiation/collection-of-light pair). An apparatus for performing image measurement for a living body with the setting of a plurality of the minimum units is proposed in Japanese Patent Application Laid-Open No. 9-98972.

It is to be noted that the distance between the light irradiation position and the collection of light position in the light-irradiation/collection-of-light pair (hereinafter referred to as the light-irradiation/collection-of-light intra-pair distance) varies with the area or depth of a region to be measured. To respond to the variation, Japanese Patent Application Laid-Open No. 9-98972 proposes an arrangement in which the optical wave-guides for light irradiation and the optical wave-guides for collection of light are alternately arranged at the points of a square lattice such that the individual light-irradiation/collection-of-light intra-pair distances are equal. If the arrangement is used, each of the optical wave-guides is used commonly by a plurality of the light-irradiation/collection-of-light pairs so that image measurement is accomplished with a smaller number of optical wave-guides. This allows short-time attachment of the optical wave-guides to a living body.

DISCLOSURE OF THE INVENTION

Although the arrangement is applied easily to such a limited region of a living body as to allow approximation with a plan surface of the living body (which is, e.g., 15 cm square in the case of measuring a head), it is difficult to the apply the arrangement to a region with a high curvature. The head configurations of new borns and infants have particularly high curvatures and large individual differences. If measurement is performed with respect to a new born or an infant, it is impossible to expect the subject to stay still so that a problem unexpectable from an adult occurs. For example, the displacement of a probe resulting from the movement of the subject should be suppressed.

Thus far, a device for measuring the activity of the brain of a new born or an infant has been limited to an electro-encephalograph. However, the electroencephalograph is not sufficiently high in spatial resolution so that it is difficult to separate data on the brain stem at the center of the brain from data on the cerebral cortex at the surface of the brain. On the other hand, a method for measuring the activity of a brain based on photometry has been expected to be extremely effective in recognizing the development process of a higher order brain function that has peculiarly developed in a human since the method allows non-invasive measurement of a cerebral cortex closely related to the higher order brain function.

Although the method has been known effective in terms of principle, a fixer (probe) for fixing the wave-guides for light irradiation and for collection of light has not been developed.

To construct a practical optical wave-guide probe for a new born or an infant, the following requirements should be satisfied, which are (1) Flexibility:

A photometric probe to be used should flexibly be adaptable to a surface of a living body with a curvature.

(2) Ability to retain distance between source wave-guide and detector wave-guide:

In a photometric probe to be used, the distance between a source wave-guide and a detector wave-guide (to be more precise, the distance between the end of the wave-guide for light irradiation and the end of the wave-guide for collection of light, which will be hereinafter referred to as the distance between source and detector) should not be changed out of a specified permissible range relative to a configuration having individual differences.

(3) Ability to follow body motion:

A photometric probe to be used should not be displaced even under a certain degree of movement.

(4) Visibility for degree of adhesion:

A photometric probe to be used should have a high visibility and perform easy control of adhesion such that the adhesion between the optical wave-guides and the surface of a living body is recognized.

(5) Amenity:

If a subject is a new born, an infant, or the like who has low adaptability to an environmental change, the head portion should not be covered completely in terms of a temperature change.

(6) Dispersing pressure:

If a subject is a new born, an infant, or the like who has a delicate head, high pressure should not be placed locally on one point.

(7) Shape retention:

To reduce a load placed on a subject, it is necessary to attach a probe within a short period of time. Accordingly, a probe to be used should have a easily changeable shape and retain its basic shape.

(8) Easiness for wearing:

For the same reason as stated in the foregoing requirement (7), a device for easily fixing a probe is necessary.

(9) Shape/size adaptability of fixing device

A fixing device should be adaptable to the configuration of the head of a subject.

(10) Pressing property of fixing device

A fixing device should be able to apply a proper pressure.

The present invention has been achieved in view of the foregoing and it is therefore an object of the present invention to provide an optical measurement device of biological tissue comprising a probe which is attachable to a moving part of a living body having a high curvature in biophotometry.

To attain the object, the present invention has provided connection between an optical wave-guide for incidence and an optical wave-guide for collection of light with a flexible material. Preferably, the flexible material is a less elastic or retractile material for the prevention of a change in distance between source and detection. For example, silicone rubber or the like is appropriate.

To attain the object, the present invention has also disposed a material having a high friction coefficient on a surface for contact with a living body. To apply a proper pressure to each of the wave guides, connection is provided between the portions at distances of 1 to 2 centimeters from the respective ends of the wave-guides by using an elastic material.

To attain the object, the present invention has removed the portion of the material for providing connection between the ends of the optical wave guides and the material for providing connection between the portions at distances of 1 to 2 cm from the ends of the optical wave-guides which are unnecessary for connection and thereby retained visibility. The problem associated with the adhesion of the optical wave-guides to a living body has been solved easily by providing connection between the portions at distances of 1 to 2 cm from the respective ends of the optical wave-guides by using an elastic material.

Thus, the present invention provides an optical measurement device of biological tissue for measuring a substance of metabolism within a subject to be measured by using a probe comprising: a device for light irradiation for irradiating the subject with light via an optical wave-guide; and a device for collection of light for collecting light irradiated from the device for light irradiation and propagated through an inside of the subject via the optical wave-guide, the probe having a plurality of optical wave-guides for the device for light irradiation and for the device for collection of light and having a portion for contact with the subject being composed of at least one member with a surface structure.

The present invention also provides an optical measurement device of biological tissue with the foregoing structure, wherein respective end portions of the optical wave-guides of the devices for light irradiation and for collection of light are supported to have a distance between the optical wave-guides in a specified permissible range at a surface for contact with the subject.

The present invention also provides an optical measurement device of biological tissue with the foregoing structure, wherein the portion of the probe for contact with the subject is composed of a plurality of members with surface structures resulting from division.

The present invention further provides an optical measurement device of biological tissue for measuring a substance of metabolism within a subject to be measured by using a probe comprising: a device for light irradiation for irradiating the subject with light via an optical waveguide; and a device for collection of light for collecting light irradiated from the device for light irradiation and propagated through an inside of the subject via the optical wave-guide, the probe having a portion for contact with the subject being composed of a plurality of members with surface structures resulting from division, a plurality of optical wave-guides for light irradiation and a plurality of optical wave-guides for collection of light being disposed on the respective members with the surface structures, the members with the surface structures being connected to each other via a flexible member.

BEST MODE FOR CARRYING OUT THE INVENTION

A description will be given hereinafter to an embodiment of the present invention.

Figure 1:
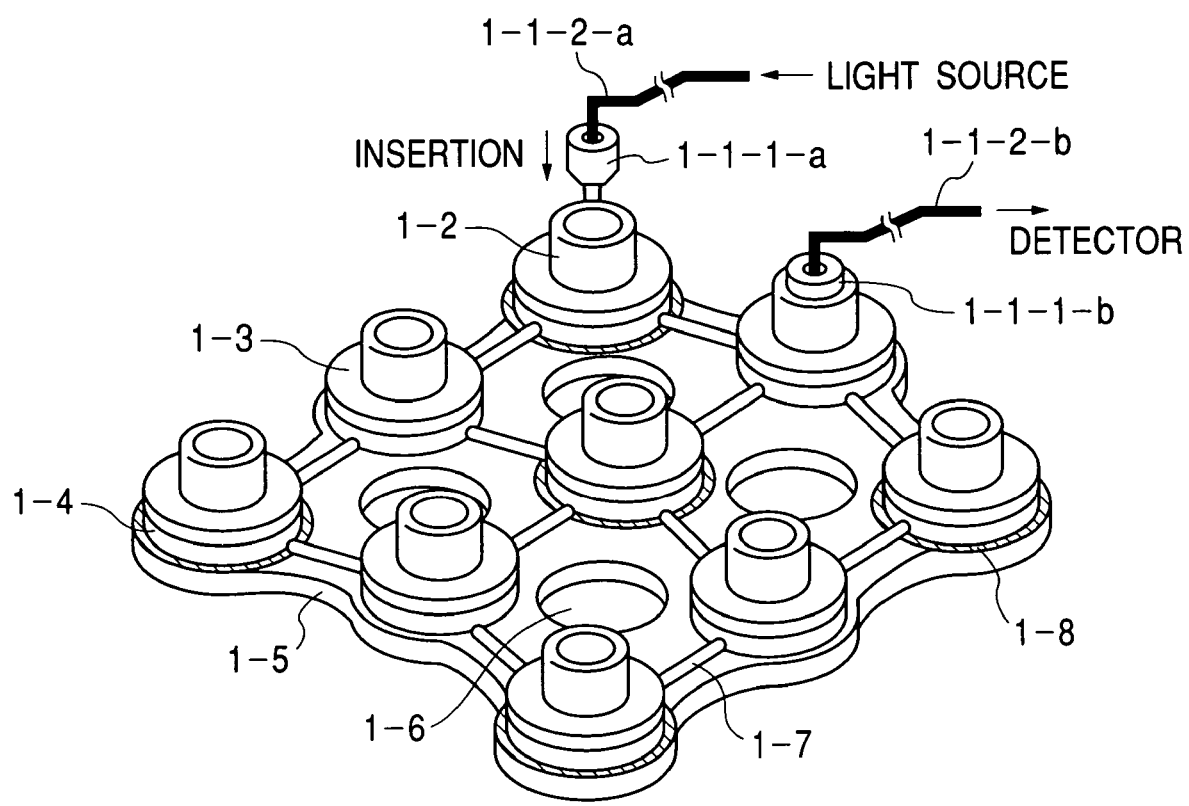
FIG. 1 is a view showing an embodiment of a part of guiding and fixing optical wave-guide of an optical probe according to the present invention.
Figure 2A:
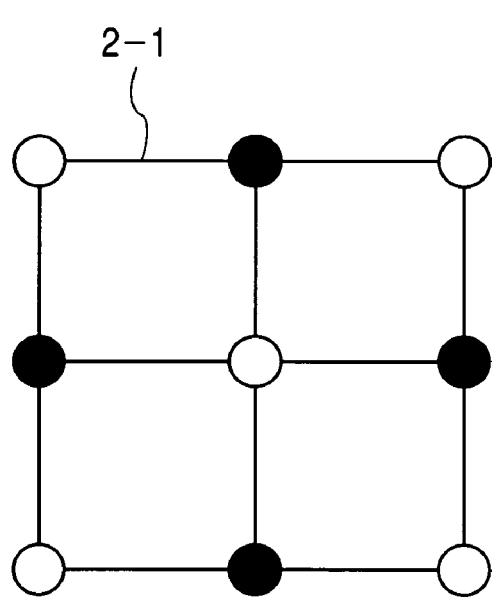
FIGS. 2(a) and 2(b) are views each showing an example of the arrangement of optical wave-guides according to the present invention.
Figure 2B:
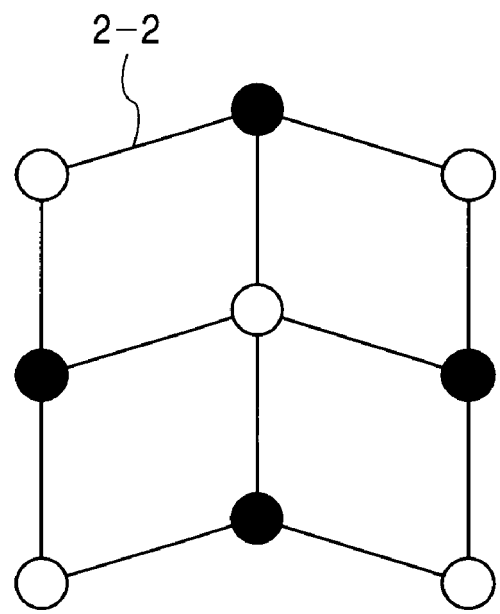

FIG. 1 shows a part of guiding and fixing optical wave-guide according to the present embodiment. FIGS. 2 show the arrangement of the optical wave-guides. FIGS. 3 show a device for attaching the part of guiding and fixing optical wave-guide to the head and a method for attachment.

The description will be given first with reference to FIG. 1. Since the part of guiding and fixing optical wave-guide is basically composed of a repetitive pattern, only a basic structure thereof will be described. An optical wave-guide for light irradiation which irradiates a subject with light from a light source is composed of a fixation part for optical wave-guide 1-1-1-a and an optical wave-guide part 1-1-2-a. The optical wave-guide is inserted in an optical wave-guide guide 1-2. In the state shown in FIG. 1, the optical wave-guide composed of a fixation part 1-1-1-b for optical wave-guide and an optical wave-guide part 1-1-2-b has already been inserted in the optical wave-guide guide 1-2 of an adjacent optical wave-guide for collection of light. Although FIG. 1 shows only one optical wave-guide prior to insertion and only one optical wave-guide after insertion, the optical wave-guide is inserted in each of the optical wave-guides in FIG. 1. Although the present embodiment shows the case where the optical wave-guides of the fixation part for optical wave-guides are nine, it will easily be appreciated that the present invention is not limited to the present embodiment.

The optical wave-guides are fixed to the optical wave-guide guides 1-2 by adhesion, by screwing, by integral processing, or by mechanical means. A joining member 1-3 for joining the optical-guide fixation guide 1-2 to a cushion member 1-4 is made of a flexible plastic and fitted in a groove formed in the optical wave-guide guide 1-2. For the cushion member 1-4, a flexible and elastic material, such as sponge or silicone, is used.

The joining member 1-3 has a bottom surface (the surface in contact with the cushion member 1-4) jointed to the cushion member 1-4 by using an adhesive or the like. The cushion member 1-4 is attached to a subject contact member 1-5 by using an adhesive or the like. Requirements placed on the subject contact member 1-5 in terms of safety are: high adaptability to the subject's tissue; a sufficient friction coefficient for the prevention of displacement resulting from body movement; no permeation or reflection of a light source wavelength for the prevention of light reflection from the surface of the subject contact member 1-5 (e.g., black color); and softness required to flexibly follow an arbitrary configuration.

A hole (aperture) 1-6 for enhancing air permeability and recognizing the state of contact with the optical wave-guides is also provided. As an example of a material which satisfies these requirements, silicone rubber or cloth can be listed. However, another material satisfying the same requirements may also be used.

A shape retaining member 1-7 is fixed to the subject contact member 1-5 in such a manner as to provide connection between the optical wave-guide guides 1-2 to each other and thereby retain an overall shape. The shape retaining member 1-7 is made of a linear metal or plastic. If the subject contact member 1-5 has sufficient rigidity or if the portion for contact with the subject has a high curvature, the provision of the shape retaining member 1-7 may also be omitted.

A filter 1-8 for light attenuation is made of a soft material such as vinyl. If the intensity of light source is high or if the intensity cannot be adjusted at a light source for light irradiation, the filter 1-8 for light attenuation is attached to cover the end portion of the optical wave-guide for light irradiation. However, the provision of the filter 1-8 for light attenuation may be omitted depending on the situation.

The end portion of the optical wave-guide is fixed to a position retracted slightly upward from the surface of the subject contact member 1-5 for contact with the subject. Preferably, the end portion is retracted upward by, e.g., about 0.5 mm to 4 mm.

The characteristics of the part of guiding and fixing optical wave-guide are listed as follows:

(1) Since the connecting member is composed of an extremely soft material, it can follow an arbitrary configuration;

(2) Since connection is provided between the end portions of the optical wave-guides, the distance between the optical wave-guides (actually a path) does not change at the portion for contact with the subject. This contributes to a constant degree of light penetration at each of measurement positions and to the acquisition of a spatially uniform signal.

(3) Since the connecting member has a proper friction coefficient, displacement does not occur even if body movement occurs.

(4) Since the unneeded portion of the connecting member is formed with the hole, visibility for checking the adhesion of the optical wave-guides is high.

(5) Since the unneeded portion of the connecting member is formed with the hole, ventilation for preventing the skin of the subject from becoming damp can be performed so that amenity is increased.

(6) Since the end portions of the optical wave-guides do not solely apply pressure to the surface of the skin of the subject, the pressure can be applied to a wide region. Moreover, the application of pressure by each of the cushion members reduces pain undergone by the subject.

The description will be given next to the arrangement of the optical wave-guides in the part of guiding and fixing optical wave-guide with reference to FIGS. 2(*a*) and 2(*b*).

Here, the respective basic structures of an arrangement 2-1 and an arrangement 2—2 are shown. The arrangement 2-1 shown in FIG. 2(*a*) is a normally used arrangement of optical wave-guides, which is used when there is no particular problem in fixing the part of guiding and fixing optical wave-guide to a living body. The optical wave-guides are positioned on the points of a square lattice. The hollow circles represent positions at which the wave-guides for light irradiation are placed. The solid circles represent positions at which the wave-guides for light detection (collection of light) are placed.

The arrangement 2—2 shown in FIG. 2(*b*) is an arrangement of optical wave-guides used when a temporal lobe is measured. Due to the presence of an ear, it is difficult in measuring the temporal lobe to arrange the optical wave-guides in a square lattice configuration. Here, the center vertical line is slightly elevated (by 1 cm to 2 cm) from the vertical lines on both sides for the avoidance of the ear. Such an arrangement allows measurement to be performed, while avoiding the ear. Specifically, the optical wave-guides are positioned on the points of a rhombic lattice. The hollow circles represent positions at which the optical wave-guides for light irradiation are placed. The solid circles represent positions at which the wave-guides for light detection (collection of light) are placed.

In each of the two arrangements, the positions of the optical wave-guides for light irradiation and those of the optical wave-guides for collection of light may be switched. If an image is reconstructed from a signal measured in the arrangement 2—2, the image is displayed in the same configuration as in the arrangement.

The description will be given next to a device and method for attaching the part of guiding and fixing optical wave-guide of an optical probe to a head with reference to FIGS. 3(*a*) to 3(*c*). FIG. 3(*a*) is a view of the part of guiding and fixing optical wave-guide when viewed from the surfaces thereof to be attached to the head. FIG. 3(*b*) is a view of the part of guiding and fixing optical wave-guides when viewed from an oblique direction. FIG. 3(*c*) is a view of the part of guiding and fixing optical wave-guide when it is attached to the head.

As shown in FIG. 3(*a*), the parts 3-1 and 3-2 of guiding and fixing optical wave-guides are held by the holding portions 3—3 and 3-4 for parts of guiding and fixing optical wave-guides. The holding portions 3—3 and 3-4 for parts of guiding and fixing optical wave-guides are composed of elastic belts or straps 3-3-1, 3-3-2, 3-3-3, 3-4-1, 3-4-2, and 3-4-3, as shown in FIG. 3(*b*). The elastic belts or straps are connected to each other at the both ends of the holding portions 3—3 and 3-4 for parts of guiding and fixing optical wave-guides.

Preferably, the elastic belts or straps are composed of light-weight and finest possible ones for easy recognition of the state of contact of the optical wave-guides. Although the present invention has used elastic cloth, a different material may also be used instead provided that it has the same functions.

The connecting portions 3-5 and 3-6 of the holding portions for parts of guiding and fixing optical wave-guides are formed to provide connection between the holding portions 3—3 and 3-4 for parts of guiding and fixing optical wave-guides. The configuration and function of each of the connecting portions 3-5 and 3-6 of the holding portions for parts of guiding and fixing optical wave-guides are determined for the following reasons.

First, the size of an object to be measured has individual differences since it is a living body. The distance of connection should be changed to respond to the individual differences. The present invention has attached Velcro straps to the both ends of the holding portions 3—3 and 3-4 for parts of guiding and fixing optical wave-guides and to the connecting portions 3-5 and 3-6 of the holding portions for parts of guiding and fixing optical wave-guides, thereby allowing distance adjustment in accordance with the circumferential length of the head.

Since the connecting portions 3-5 and 3-6 of the holding portions for parts of guiding and fixing optical wave-guides are brought into direct contact with the skin of the subject, consideration should be given to the widths thereof and to the surfaces thereof for contact with the subject. To avoid the localization of pressure to the skin of the subject, the connecting portions 3-5 and 3-6 should not have their widths minimized, which is different from the elastic belts or straps composing the holding portions 3—3 and 3-4 for parts of guiding and fixing optical wave-guides. It is necessary for the connecting portions 3-5 and 3-6 to have certain widths preferably ranging from 1 cm to 4 cm. The surfaces of the connecting portions 3-5 and 3-6 of the holding portions for parts of guiding and fixing optical wave-guides for contact with the subjects are preferably made of a soft material having a high friction coefficient (for the prevention of slippage). As an example of the material, silicone rubber or sponge can be listed. It will easily be understood that another material may also be used provided that it has the same functions.

If the parts 3-1 and 3-2 of guiding and fixing optical wave-guides are small, attachment by using the components described above is possible. If the parts 3-1 and 3-2 of guiding and fixing optical wave-guides are large, however, it is necessary to uniformly apply pressure to each of the optical wave-guides by using auxiliary holding portions, which will be described below.

Figure 3A:
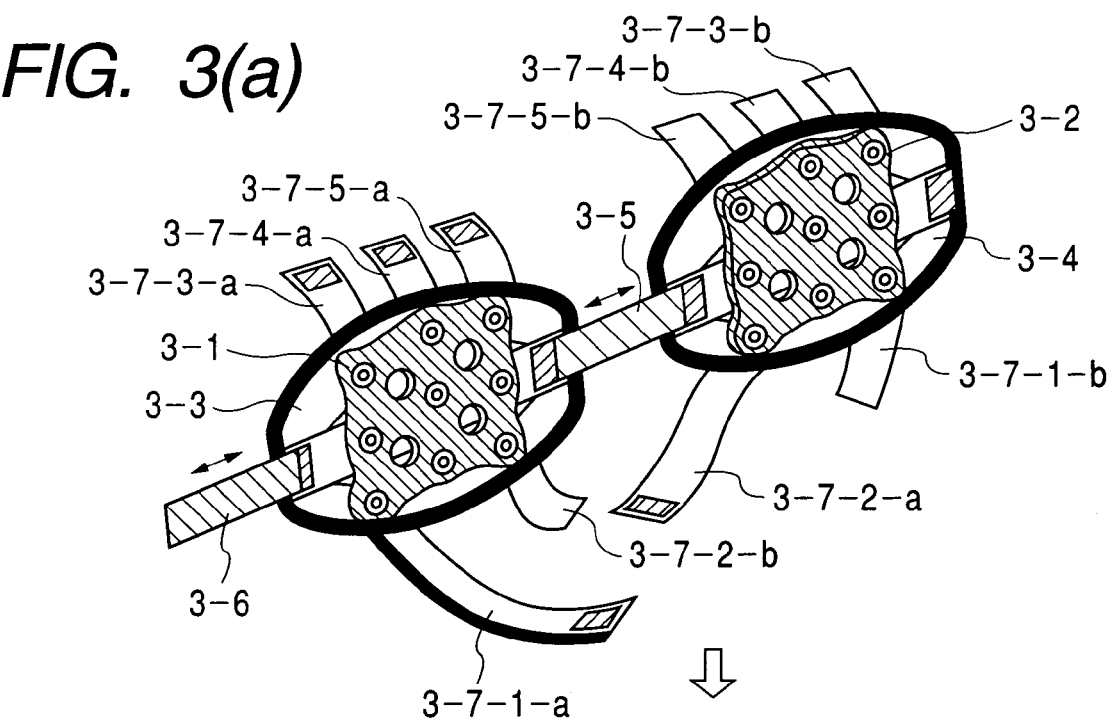
FIGS. 3(a) to 3(c) are views illustrating a device and method for attaching an optical probe according to the present invention.
Figure 3B:
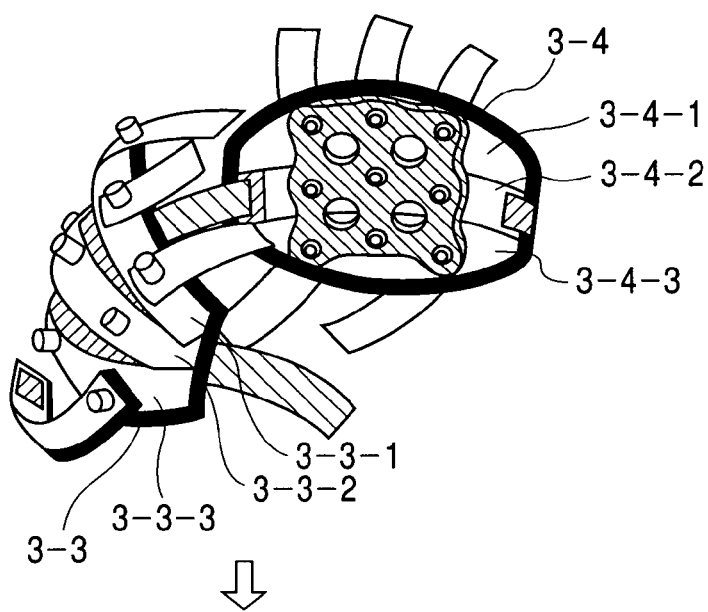

As shown in FIG. 3(a), the present invention has attached auxiliary holding portions 3-7-1-a to 3-7-5-a and 3-7-1-b to 3-7-5-b. To the end of each of the auxiliary holding portions 3-7-1-a to 3-7-5-a and 3-7-1-b to 3-7-5-b, a Velcro strap has been attached. For example, the auxiliary holding portions 3-7-1-a and 3-7-1-b are connected to each other by adjusting the lengths thereof in accordance with the configuration of the head of the subject. The other auxiliary connecting portions a and b forming pairs are similarly connected by adjusting the lengths thereof. As the materials of the auxiliary holding portions 3-7-1-a to 3-7-5-a and 3-7-1-b to 3-7-5-b, finest possible elastic bands or straps are used.

Figure 3C:
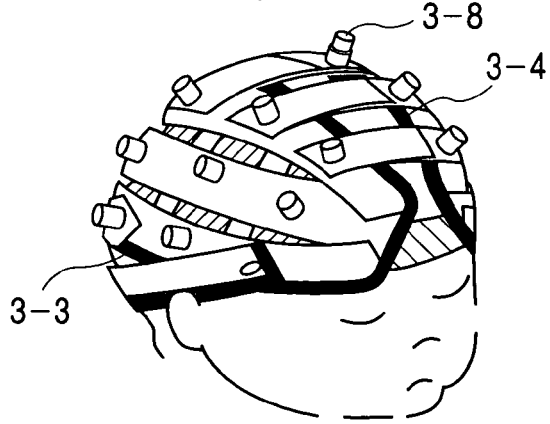

As shown in FIG. 3(c), the optical wave-guides are inserted in all the optical wave-guide guides, similarly to the optical wave-guide 3-8. Easy attachment can be accomplished by following the procedure shown in FIG. 3(a), 3(b), and 3(c) in this order.

The characteristics of the holding portions for parts of guiding and fixing optical wave-guides are as follows.

(1) Easy and quick attachment (2) Adaptability to the configurations and sizes of the various measured parts of a subject (3) Ability to apply uniform and proper pressure to the skin of a subject Although the configurations of the holding portions for parts of guiding and fixing optical wave-guides vary depending on the part to be measured, the essential characteristics required of the structure of the holding portion for part of guiding and fixing optical wave-guide is as follows:

(1) The holding portion is divided into a plurality of parts which are connected to each other upon attachment.

(2) Connecting portions are designed to allow length adjustment.

(3) Elastic belts or straps are used.

To realize the foregoing (1) and (2), a Velcro strap, e.g., is used. To realize the foregoing (3), elastic cloth, rubber, or the like is used.

Figure 4:
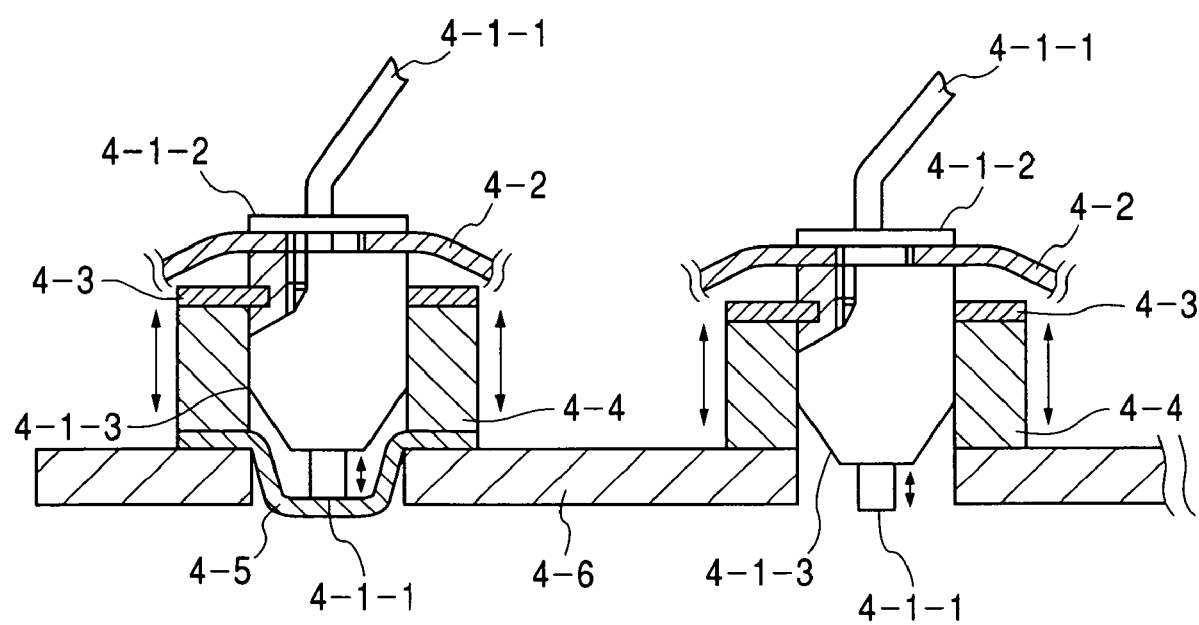
FIG. 4 is a cross-sectional view of the optical wave-guide fixing portion of the optical probe according to the present invention.

FIG. 4 shows a cross-sectional view of the parts of guiding and fixing optical wave-guides of the optical probe. The optical wave-guide is basically composed of an optical wave-guide portion 4-1-1, a cap 4-1-2 for fixation part for optical wave-guide, and a fixation part 4-1-3 for optical wave-guide. The optical wave-guide portion 4-1-1 extends through the fixation part 4-1-3 for optical wave-guide to have an end portion protruding, as shown in the drawing. As indicated by the arrow, the end portion is vertically movable under arbitrary pressure (an elastic element is disposed in the fixation part 4-1-3 for optical wave-guide). Owing to the vertical movability, the end portion of the optical wave-guide is brought into close contact with the surface of the subject under proper pressure.

The cap 4-1-2 for fixation part for optical wave-guide and the fixation part 4-1-3 for optical wave-guide are connected to each other via screws formed in the outer wall surface of the fixation part 4-1-3 for optical wave-guide and in the inner wall surface of the cap 4-1-2 for fixation part for optical wave-guide.

Fixation is achieved by an elastic belt or strap 4-2 composing the holding portion 3—3 or 3-4 for part of guiding and fixing optical wave-guide shown in FIGS. 3 which is sandwiched between the cap 4-1-2 for fixation part for optical wave-guide and the fixation part 4-1-3 for optical wave-guide. If the elastic belt or strap is extremely thin, it may be formed into a ring configuration and sandwiched in the same manner as described above or may be fixed by a fixing portion which is provided in the fixation part for optical wave-guide or in the optical wave-guide guide.

A joining member 4-3 made of plastic to have a ring configuration joins a cushion member 4—4 composing the optical wave-guide guide to the fixation part 4-1-3 for optical wave-guide composing the optical wave-guide. The joining member 4-3 has a lower surface joined to the cushion member 4—4 with an adhesive. As shown in the drawing, the hole formed in the joining member 4-3 is fitted in the groove of the fixation part 4-1-3 for optical wave-guide. If the optical wave-guide and the optical wave-guide guide can be formed integrally by integral molding or by adhesion, the joining member 4-3 is no more necessary. As shown in the drawing, the cushion member 4—4 is movable in the direction (vertical) indicated by the arrow and receives proper pressure applied by the elastic belt or strap 4-2 composing the holding portion for part of guiding and fixing optical wave-guide.

There are cases where a filter 4-5 for light attenuation is attached to cover the end portion of the optical wave-guide for light irradiation.

The optical wave-guide guide and the optical wave-guide are connected to each other by a subject contact member 4-6. Preferably, the thickness of the subject contact member 4-6 is minimized. The subject contact member 4-6 is black in color, has a high friction coefficient relative to the subject's tissue, and is disposed on the near end portion of the optical wave-guide portion 4-1-1. If the subject contact member 4-6 has high perspiration and high air permeability, amenity can further be increased.

Although the description of the foregoing embodiment has been given primarily to the measurement of the head of a new born or an infant, the present invention is not limited to the measurement of the head of a new born or an infant. By changing the size and the arrangement of optical wave-guides, while retaining the components, the present invention is also applicable to the measurement of the head of an adult or to the in-organism measurement of a muscle other than the head.

By thus implementing a double structure or layer in which the member high in flexibility and friction coefficient is disposed on the surface for contact with a living body and the device for light irradiation and the device for collection of light are fixed by using the elastic material for uniform application of pressure to the surface for contact, the present invention has enabled biophotometry for a moving part of a living body.

INDUSTRIAL APPLICABILITY

The present invention has enabled measurement for a moving part such as the head or arm of a new born or an infant, which has conventionally been difficult to measure, by using an optical probe easily attachable to the surface of a living body having a high curvature. The present invention has also expanded the range of applications of an optical measurement device of biological tissue and made a great industrial contribution. In particular, the understanding of the development process of brain activity contributes to a field greatly affecting a human society, such as education.

What is claimed is:

1. An optical measurement device of biological tissue for measuring a substance of metabolism within a subject to be measured by using a probe comprising:
   a device for light irradiation for irradiating the subject with light via an optical wave-guide; and
   a device for collection of light for collecting light irradiated from the device for light irradiation and propagated through an inside of the subject via another optical wave-guide,
   said probe having a plurality of guides, each of said guides fixing a respective one of said optical wave-guides, and having a portion for contact with said subject being composed of at least one member with a surface structure, said portion for contact with said subject being made of flexible material, said guides being fixed to said portion for contact with said subject so that the respective ends of said optical wave-guides contact with a surface of said subject when said device is worn, and having a holding portion which connects and holds each said optical wave-guide.

2. The optical measurement device of biological tissue of claim 1, wherein respective end portions of the optical wave-guides of said devices for light irradiation and for collection of light are supported to have a distance between the optical wave-guides in a specified permissible range at a surface for contact with said subject.

3. The optical measurement device of biological tissue of claim 1, wherein said portion for contact with said subject is composed of a material having a high flexibility and a high friction coefficient.

4. The optical measurement device of biological tissue of claim 1, wherein said portion for contact with said subject is composed of a material which does not permeate or reflect a wavelength of said light.

5. The optical measurement device of biological tissue of claim 1, wherein a region of said member with the surface structure for contact with said subject which is surrounded by said optical wave-guides is provided with an aperture.

6. The optical measurement device of biological tissue of claim 1, wherein an end portion of said device for light irradiation is covered with a filter for light attenuation.

7. The optical measurement device of biological tissue of claim 1, wherein each of said devices for light irradiation and for collection of light has four or more optical wave-guides.

8. The optical measurement device of biological tissue of claim 1, wherein an end portion of each of said devices for light irradiation and for collection of light is vertically movable above a surface of the subject.

9. The optical measurement device of biological tissue of claim 1, wherein said devices for light irradiation and for collection of light are alternately positioned at points of a square lattice configuration or a rhombic lattice configuration.

10. The optical measurement device of claim 1, further comprising a plurality of members connected with each other so as to mount said probe on said subject.

* * * * *